United States Patent
Li et al.

(10) Patent No.: US 11,628,311 B2
(45) Date of Patent: Apr. 18, 2023

(54) TUMOR POSITIONING METHOD AND APPARATUS

(71) Applicants: OUR UNITED CORPORATION, Xi'an (CN); SHENZHEN OUR NEW MEDICAL TECHNOLOGIES DEVELOPMENT CO., LTD., Shenzhen (CN)

(72) Inventors: Jiuliang Li, Xi'an (CN); Hao Yan, Xi'an (CN); Zhongya Wang, Xi'an (CN)

(73) Assignees: OUR UNITED CORPORATION, Xi'an (CN); SHENZHEN OUR NEW MEDICAL TECHNOLOGIES DEVELOPMENT CO., LTD., Shenzhen (CN)

( * ) Notice: Subject to any disclaimer, the term of this patent is extended or adjusted under 35 U.S.C. 154(b) by 102 days.

(21) Appl. No.: 17/171,460

(22) Filed: Feb. 9, 2021

(65) Prior Publication Data
US 2021/0162235 A1 Jun. 3, 2021

Related U.S. Application Data

(63) Continuation-in-part of application No. PCT/CN2018/100103, filed on Aug. 10, 2018.

(51) Int. Cl.
*A61N 5/10* (2006.01)

(52) U.S. Cl.
CPC .... *A61N 5/1048* (2013.01); *A61N 2005/1062* (2013.01)

(58) Field of Classification Search
CPC .......... A61N 5/00; A61N 5/10; A61N 5/1048; A61N 5/1049; A61N 2005/1062; A61N 2005/1061
See application file for complete search history.

(56) References Cited

U.S. PATENT DOCUMENTS

| 9,227,087 B2 | 1/2016 | Marash et al. |
| 2007/0127845 A1 | 6/2007 | Fu et al. |

(Continued)

FOREIGN PATENT DOCUMENTS

| CN | 101843954 A | 9/2010 |
| CN | 102222331 A | 10/2011 |

(Continued)

OTHER PUBLICATIONS

International Search Report and Written Opinion issued in corresponding International Application No. PCT/CN2018/100103 dated May 17, 2019, with English translation.

(Continued)

*Primary Examiner* — Jurie Yun
(74) *Attorney, Agent, or Firm* — Morgan, Lewis & Bockius LLP

(57) ABSTRACT

A tumor positioning method includes obtaining projection images of a tumor at different angles; and registering the projection images with an initial reference image to obtain a first offset. If it is determined that a virtual reacquisition operation needs to be performed according to the first offset, the method further includes generating a first reference image according to the first offset; and registering the projection images with the first reference image to obtain a second offset. If it is determined that the operation does not need to be performed according to the second offset, the method further includes outputting a first accumulated offset being a sum of the first and second offsets. The method may solve problems of long time consuming and the service life of a treatment couch and acquisition devices being reduced due to repeatedly moving the treatment couch and repeatedly acquiring the X-ray projection images.

14 Claims, 3 Drawing Sheets

(56) References Cited

U.S. PATENT DOCUMENTS

| | | |
|---|---|---|
| 2008/0037843 A1 | 2/2008 | Fu et al. |
| 2009/0175406 A1 | 7/2009 | Zhang et al. |
| 2010/0246915 A1 | 9/2010 | Yamakoshi et al. |
| 2011/0194745 A1 | 8/2011 | Dafni et al. |
| 2012/0035462 A1 | 2/2012 | Maurer, Jr. et al. |
| 2013/0163724 A1 | 6/2013 | Marash et al. |
| 2014/0205167 A1 | 7/2014 | Kleiner |
| 2014/0228678 A1 | 8/2014 | Meyer et al. |
| 2015/0352376 A1 | 12/2015 | Wiggers et al. |
| 2016/0335777 A1 | 11/2016 | Borsdorf et al. |

FOREIGN PATENT DOCUMENTS

| | | |
|---|---|---|
| CN | 102440789 A | 5/2012 |
| CN | 104587609 A | 5/2015 |
| DE | 10 2015 208 929 B3 | 6/2016 |
| EP | 1 674 286 A1 | 6/2006 |
| JP | 2009-189461 A | 8/2009 |
| JP | 2013-99431 A | 5/2013 |
| JP | 2016-152992 A | 8/2016 |
| WO | 2011/156526 A2 | 12/2011 |
| WO | 2018/129374 A1 | 7/2018 |

OTHER PUBLICATIONS

Extended European Search Report issued in corresponding European Patent Application No. 18929819.3 dated Feb. 23, 2022.
Office Action issued in corresponding Chinese Patent Application No. 2018800955273 dated May 23, 2022, with English translation.

TUMOR POSITIONING METHOD AND APPARATUS

CROSS-REFERENCE TO RELATED APPLICATION

This application is a Bypass Continuation-in-Part application of PCT/CN2018/100103 filed on Aug. 10, 2018, which is incorporated herein by reference in its entirety.

TECHNICAL FIELD

Embodiments of the present disclosure relate to the field of radiotherapy, and in particular, to a tumor positioning method and apparatus.

BACKGROUND

Radiotherapy, one of the main means for treating malignant tumors, may position a tumor and cause apoptosis of cancer cells at the position through radiation. If there is a deviation when the tumor is positioned, it will not only cause the cancer cells to not be effectively killed, but also increase a risk of secondary cancer. Therefore, it is very important to accurately position the tumor before and during radiotherapy.

SUMMARY

In a first aspect, embodiments of the present disclosure provide a tumor positioning method. The method include: obtaining projection images of a tumor at different angles; and registering the projection images with an initial reference image to obtain a first offset of the tumor. If it is determined that a virtual reacquisition operation needs to be performed according to the first offset, the method further includes: generating a first reference image according to the first offset; and registering the projection images with the first reference image to obtain a second offset of the tumor. If it is determined that the virtual reacquisition operation does not need to be performed according to the second offset, the method further includes: outputting a first accumulated offset, the first accumulated offset being a sum of the first offset and the second offset.

In some embodiments, if it is determined that the virtual reacquisition operation needs to be performed according to the second offset, the method further includes: generating a second reference image according to a first accumulated offset, the first accumulated offset being a sum of the first offset and the second offset; and registering the projection images with the second reference image to obtain a third offset of the tumor. If it is determined that the virtual reacquisition operation does not need to be performed according to the third offset, the method further includes: outputting a second accumulated offset, the second accumulated offset being a sum of the first offset, the second offset and the third offset.

In some embodiments, determining that the virtual reacquisition operation needs to be performed includes: determining that an offset is not within a preset offset range, or receiving an instruction that it is determined that the virtual reacquisition operation needs to be performed according to an offset. The offset is the first offset, the second offset or the third offset.

In some embodiments, after determining an accumulated offset, the method further includes: displaying the accumulated offset. The accumulated offset is the first accumulated offset or the second accumulated offset.

In some embodiments, generating the first reference image includes: generating the first reference image through a preset algorithm according to the first offset and pre-stored geometric information.

In some embodiments, generating the second reference image includes: generating the second reference image through a preset algorithm according to the first accumulated offset and pre-stored geometric information.

In some embodiments, the initial reference image includes a computed tomography (CT) image. Registering the projection images with the initial reference image to obtain the first offset includes: reconstructing the projection images at the different angles to obtain a target image with same dimensions as the CT image; and registering the target image with the CT image to obtain the first offset.

In some embodiments, the initial reference image includes digitally reconstructed radiograph (DRR) images each corresponding to a respective one of the projection images at the different angles. Registering the projection images with the initial reference image to obtain the first offset includes: registering the projection images with the DRR images to obtain two-dimensional offsets of the tumor; and obtaining the first offset according to the two-dimensional offsets.

In some embodiments, the tumor positioning method further includes obtaining the initial reference image before obtaining the projection images.

In a second aspect, embodiments of the present disclosure provide a tumor positioning method. The method includes: obtaining projection images of a tumor at different angles; generating initial reference images at angles corresponding to the projection images according to an initial image; and registering the projection images with the initial reference images to obtain a first offset of the tumor. If it is determined that the first offset is not within a preset offset range, the method further comprises: generating first reference images at corresponding angles according to the first offset and the initial image; and registering the projection images at the different angles with the first reference images at the corresponding angles to obtain a second offset of the tumor. If it is determined that the second offset is within the preset offset range, the method further comprises: outputting a first accumulated offset, the first accumulated offset being a sum of the first offset and the second offset.

In some embodiments, If it is determined that the second offset is not within the preset offset range, the method further comprises: generating second reference images at the corresponding angles according to the first accumulated offset and the initial image; and registering the projection images at the different angles with the second reference images at the corresponding angles to obtain a third offset of the tumor. If it is determined that the third offset is within the preset offset range, the method further comprises: outputting a second accumulated offset, the second accumulated offset being a sum of the first offset, the second offset and the third offset.

In some embodiments, the initial image includes a computed tomography (CT) image; and the initial reference images are digitally reconstructed radiograph (DRR) images each corresponding to a respective one of the projection images at the different angles.

In a third aspect, embodiments of the present disclosure provide a tumor positioning apparatus. The tumor positioning apparatus includes a processor and a memory. The memory is configured to store computer execution instructions, and when the tumor positioning apparatus is running, the processor is configured to execute the computer execution instructions stored in the memory to cause the tumor positioning apparatus to perform the tumor positioning method according to the first aspect or the second aspect.

In a fourth aspect, embodiments of the present disclosure provide a non-transitory computer-readable storage medium storing computer execution instructions that, when executed by a computer, cause the computer to perform the tumor positioning method according to the first aspect or the second aspect.

DETAILED DESCRIPTION

Figure 1:
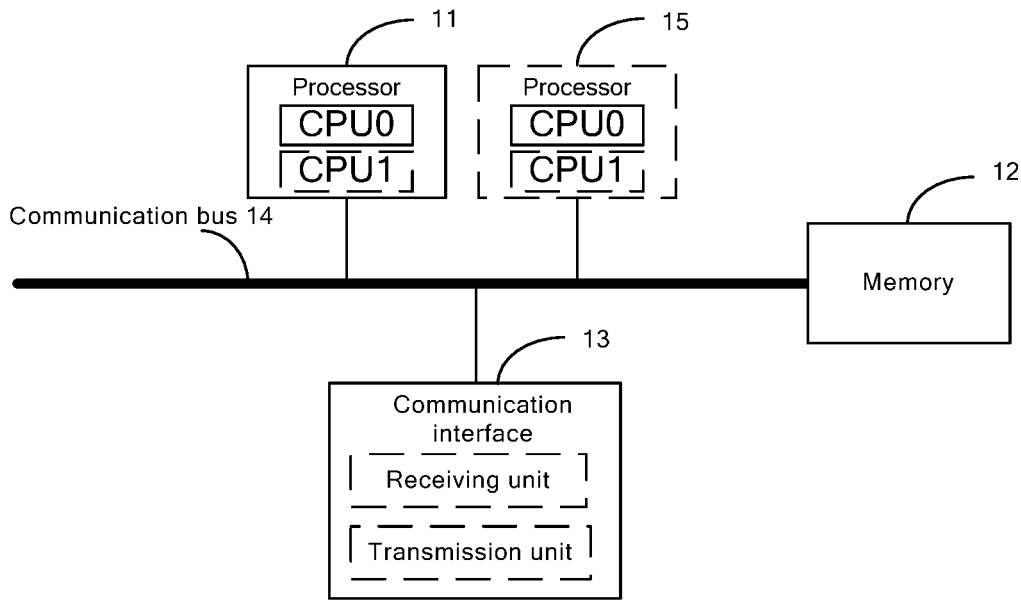
FIG. 1 is a schematic diagram showing components of a tumor positioning apparatus, in accordance with embodiments of the present disclosure.

Technical solutions in embodiments of the present disclosure will be described below clearly and completely in combination with accompanying drawings in embodiments of the present disclosure. Obviously, the described embodiments are merely some but not all embodiments. All other embodiments obtained by a person of ordinary skill in the art based on the embodiments of the present disclosure without paying any creative effort shall be included in the protection scope of embodiments of the present disclosure.

Unless the context requires otherwise, throughout the specification and claims which follow, the word "comprise" and variations thereof, such as, "comprises" and "comprising" are to be construed in an open, inclusive sense, that is as "including, but not limited to." In the description of the description, terms such as "one embodiment", "some embodiments", "exemplary embodiments", "example", "specific example" or "some examples" are intended to indicate that specific features, structures, materials or characteristics related to the embodiment(s) or example(s) are included in at least one embodiment or example of the present disclosure. Schematic representations of the above terms do not necessarily refer to the same embodiment or example. In addition, the specific features, structures, materials or characteristics may be included in any one or more embodiment(s) or example(s) in any suitable manner.

As following, the terms "first" and "second" are used for descriptive purposes only and are not to be construed as indicating or implying the relative importance or implicitly indicating the number of indicated technical features. Thus, features defined as "first" or "second" may explicitly or implicitly include one or more of the features. As used in this specification and the appended claims, the singular forms "a," "an," and "the" include plural referents unless the content clearly dictates otherwise. In the description of the embodiments of the present disclosure, the term "a/the plurality of" means two or more unless otherwise specified.

Some embodiments may be described using the expression "coupled" and "connected" along with their derivatives. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled" or "communicatively coupled," however, may also mean that two or more elements are not in direct contact with each other, but yet still co-operate or interact with each other. The embodiments disclosed herein are not necessarily limited in this context.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

The use of "adapted to" or "configured to" herein is meant as open and inclusive language that does not foreclose devices adapted to or configured to perform additional tasks or steps.

Additionally, the use of "based on" is meant to be open and inclusive, in that a process, step, calculation, or other action "based on" one or more recited conditions or values may, in practice, be based on additional conditions or value beyond those recited.

Generally, the tumor is positioned through X-ray projection image guidance, which specifically includes: acquiring X-ray projection images at different angles (for example 0 degrees and 90 degrees) though devices such as a detector, and an X-ray tube; and registering the X-ray projection images acquired at different angles with corresponding digitally reconstructed radiograph (DRR) images to obtain an offset. The DRR images are generated according to a computed tomography (CT) image in a treatment plan. If the offset is not within a preset range, a treatment couch is moved according to the offset. After moving, X-ray projection images are reacquired at the different angles and are registered with corresponding DRR images to obtain a new offset. If the new offset is still not within the preset range, the treatment couch is continued to be moved, and X-ray projection images are reacquired at different angles to obtain a new offset until the new offset is within the preset range.

When the tumor is positioned, the treatment couch needs to be moved repeatedly, and X-ray projection images at different angles are acquired repeatedly. In this way, it not only takes a long time, and affects the user's treatment experience, but also shortens the service life of the treatment couch and the devices such as the detector, and the tube in the X-ray machine.

FIG. 1 is a schematic diagram showing components of a tumor positioning apparatus, in accordance with embodiments of the present disclosure. As shown in FIG. 1, the tumor positioning apparatus may include: at least one processor 11, a memory 12, a communication interface 13, and a communication bus 14.

The components of the tumor positioning apparatus will be specifically described below with reference to FIG. 1.

The processor 11 is a control center of the tumor positioning apparatus, which may be a processor or a collective name for a plurality of processing elements. For example, the processor 11 may be a central processing unit (CPU), or an application specific integrated circuit (ASIC), or is configured to implement one or more integrated circuits of the embodiments of the present disclosure, such as one or more digital signal processors (DSP), or one or more field programmable gate arrays (FPGA).

In a specific implementation, as an embodiment, the processor 11 may include one or more CPUs, such as a CPU0 and a CPU1 shown in FIG. 1. Moreover, as an embodiment, the tumor positioning apparatus may include a plurality of processors, such as the processor 11 and a processor 15 shown in FIG. 1. Each of these processors may be a single-CPU or a multi-CPU. The processor here may refer to one or more devices, circuits, and/or processing cores configured to process data (such as computer program instructions).

The memory 12 may be a read-only memory (ROM) or other types of static storage devices that may store static information and instructions, a random access memory (RAM) or other types of dynamic storage devices that may store information and instructions, or electrically erasable programmable read-only memory (EEPROM), compact disc read-only memory (CD-ROM), or other disc storage, optical disc storage (including compact discs, laser discs, optical discs, digital versatile discs, blue-ray discs, etc.), disk storage media or other magnetic storage devices, or any other medium that is configured to carry or store expected program codes in a form of instructions or data structures and can be accessed by a computer, which is not limited thereto. The memory may exist independently and be connected to the processor 11 through the communication bus 14. The memory 12 may also be integrated with the processor 11.

In an implementation, the memory 12 is configured to store data in embodiments of the present disclosure and executing software programs in embodiments of the present disclosure. The processor 11 may perform various functions of the tumor positioning apparatus by running or executing the software programs stored in the memory 12 and invoking the data stored in the memory 12.

The communication interface 13 may use a device such as a transceiver, and is configured to communicate with other devices or communication networks, such us a control system, a radio access network (RAN), or wireless local area networks (WLAN). The communication interface 13 may include a receiving unit to realize a receiving function, and a transmission unit to realize a transmission function.

The communication bus 14 may be an industry standard architecture (ISA) bus, a peripheral component interconnect (PCI) bus, an extended industry standard architecture (EISA) bus, or the like. The bus may be classified into an address bus, a data bus, and a control bus, etc. For convenience of representation, only one thick line is used to represent the bus in FIG. 1, but it does not mean that there is only one bus or one type of buses.

Figure 2A:
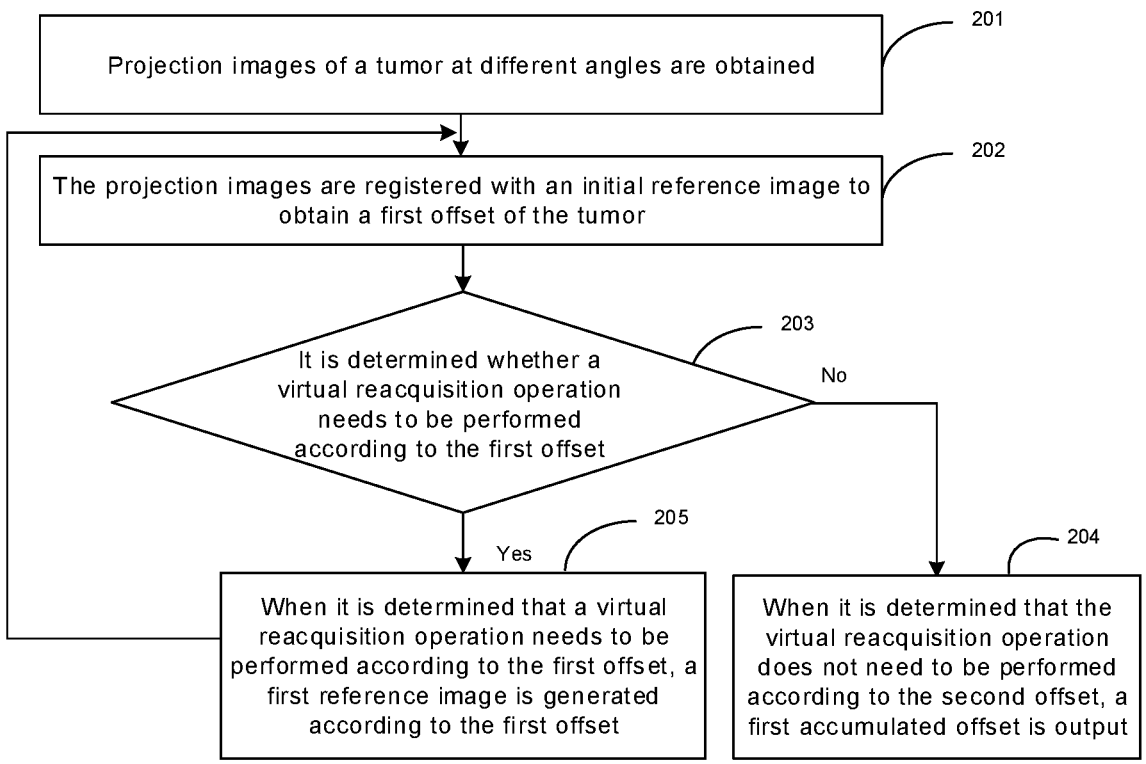
FIG. 2A is a flow diagram of a tumor positioning method, in accordance with embodiments of the present disclosure.

In order to solve the problems of long time consuming and the service life of the treatment couch and the devices such as the detector, and the tube being reduced due to repeatedly moving the treatment couch and repeatedly acquiring the X-ray projection images at different angles, the embodiments of the present disclosure provide a tumor positioning method. As shown in FIG. 2A, the method may include the following steps.

In S201, projection images of the tumor at different angles are obtained.

When there is a need to position the tumor, the tumor positioning apparatus may obtain an initial reference image, and obtain the projection images of the tumor at different angles according to pre-stored geometric information.

Herein, the initial reference image is generally an image for formulating a tumor treatment plan. The image includes information such as a contour of the tumor's target area. The geometric information includes angle information for obtaining the projection images.

In an implementation, the projection images may be two-dimensional images, such as KV-level X-ray projection images. In another implementation, the projection images may also be three-dimensional images, such as three-dimensional images generated after reconstruction of the two-dimensional images of the tumor at the different angles.

In embodiments of the present disclosure, KV-level X-ray projection images of the tumor acquired at two angles (such as 0 degrees and 90 degrees, or two other different angles) are used as an example for description. For example, the tumor positioning apparatus may use the following two manners to obtain the KV-level X-ray projection images at two angles.

In manner one, in a case where a device for acquiring X-ray projection images is a single flat panel detector, the tumor positioning apparatus may control the flat panel detector to acquire a KV-level X-ray projection image at a first angle according to first angle information included in the geometric information, and control the flat panel detector to rotate to a second angle following a gantry that fixes the flat panel detector and to acquire a KV-level X-ray projection image at the second angle according to second angle information.

In manner two, in a case where the device for acquiring X-ray projection images is a dual flat panel detector, the tumor positioning apparatus may control a first flat panel detector to acquire the KV-level X-ray projection image at the first angle according to the first angle information included in the geometric information, and control a second flat panel detector to acquire the KV-level X-ray projection image at the second angle according to the second angle information (forming a preset angle with the first angle, such as 90 degrees), so as to obtain the KV-level X-ray projection images at the two angles.

In S202, the projection images are registered with an initial reference image to obtain a first offset of the tumor.

After obtaining the initial reference image and obtaining the projection images of the tumor at the different angles, the tumor positioning apparatus may register the projection images with the initial reference image to obtain the first offset of the tumor. The initial reference image may include a three-dimensional computed tomography (CT) image in a treatment plan, two-dimensional digitally reconstructed radiograph (DRR) images that are generated according to the CT image, each of which corresponds to a respective one of the projection images at the different angles, a magnetic resonance imaging (MRI) image, a positron emission computed tomography (PET) image, or the like.

For example, in an implementation, when the initial reference image includes the CT image, the tumor positioning apparatus registering the initial reference image with the obtained projection images to obtain the first offset of the tumor includes the following steps. The tumor positioning apparatus reconstructs the projection images of the tumor obtained at the different angles to obtain a target image. Dimensions of the target image are the same as dimensions of the CT image, and the CT image is registered with the target image to obtain the first offset of the tumor.

In another implementation, when the initial reference image includes the DRR images. The tumor positioning apparatus registering the initial reference images with the obtained projection images to obtain the first offset of the tumor, includes the following steps. The tumor positioning apparatus registers the projection images at the different angles with corresponding DRR images to obtain two-dimensional offsets at the different angles, and calculates the first offset according to the two-dimensional offsets at the different angles. The first offset may be any one of a three-dimensional offset, a four-dimensional offset, a five-dimensional offset, and a six-dimensional offset.

In S203, whether a virtual reacquisition operation needs to be performed is determined according to the first offset.

Herein, the term "virtual reacquisition" refers to virtual (hypothetical) reacquisition of the projection images of the tumor at the above different angles, rather than actual acquisition.

After the tumor positioning apparatus determines the first offset, whether the virtual reacquisition operation needs to be performed may be determined according to the first offset. In an implementation, the tumor positioning apparatus may uses an automatic manner and a manual manner to determine whether the virtual reacquisition operation needs to be performed.

In the manual manner, the tumor positioning device may perform the following step 204 after receiving an instruction from the operator that it is determined that the virtual reacquisition operation does not need to be performed according to the first offset. The tumor positioning device may also perform the following step 205 after receiving an instruction that the operator determines that the virtual reacquisition operation needs to be performed according to the first offset; and perform the following step 204 when receiving an instruction from the operator that it is determined that the virtual reacquisition operation does not need to be performed according to the first offset.

In the automatic manner, the tumor positioning device may determine whether the virtual reacquisition operation needs to be performed by determining whether the first offset is within a preset offset range. If the first offset is within the preset offset range, it is determined that the virtual reacquisition operation does not need to be performed, and in this case, the following step 204 may be performed. If the first offset is not within the preset offset range, it is determined that the virtual reacquisition operation needs to be performed, and in this case, the following step 205 may be performed.

Herein, the preset offset range means that a position offset between a target object of the obtained X-ray projection images and a target object of the DRR images at corresponding angles is within a certain range, which has no effect on positioning the tumor to kill cells in the tumor through radiotherapy. The target object may include one or more of the tumor, bone markers, or other metal markers implanted in the tumor patient in advance.

For example, the preset offset range is from 0 mm to 1 mm, that is, an offset range of the target object in each of the X, Y, and Z directions in the three-dimensional space is from 0 mm to 1 mm. It will be understood that values of the preset offset range are only for reference. In actual position, the values of the preset offset range may be set according to parameters such as tumor volume and radiotherapy accuracy. For example, the preset offset range is from 0 mm to 0.8 mm, or the preset offset range is from 0 mm to 1.2 mm.

In S204, when it is determined that the virtual reacquisition operation does not need to be performed according to the first offset, the first offset is output.

After it is determined that the virtual reacquisition operation does not need to be performed, the tumor positioning apparatus may output the first offset, and correct the position of the tumor according to the first offset, such as controlling the treatment couch to move.

In S205, when it is determined that the virtual reacquisition operation needs to be performed according to the first offset, a first reference image is generated according to the first offset.

That is, when it is determined that the virtual reacquisition operation needs to be performed according to the first offset, a new reference image relative to the above initial reference image is generated according to the first offset. The reference image generated afterwards is referred to as the first reference image to distinguish it from the initial reference image.

When it is determined that the virtual reacquisition operation needs to be performed, the tumor positioning apparatus may generate the first reference image through a preset algorithm according to the first offset and the pre-stored geometric information.

For example, when the reference images are the DRR images, the tumor positioning apparatus may generate DRR images through a DRR algorithm, each of which corresponding to a respective one of the projection images at the different angles, according to the first offset, the CT image and the pre-stored geometric information.

When the reference image is the CT image, the tumor positioning apparatus may move a reference position of the CT image in the three-dimensional space according to the first offset. That is, assuming that a position of the initial reference image in step 202 is the reference position, the reference position of the CT image is compensated according to the first offset to obtain a new reference position of the CT image, and a new reference image (i.e., the first reference image) is generated. A calculation process of compensating the reference position of the CT image according to the offset is the above preset algorithm.

On the basis above, the tumor positioning apparatus may register the projection images acquired in step 201 with the generated first reference image (i.e., a new reference image generated relative to the above initial reference image) according to step 202 to obtain a second offset, and determine a first accumulated offset. The first accumulated offset is a sum of the first offset and the second offset. Then, according to step 203, it is determined whether the virtual reacquisition operation needs to be performed according to the second offset. If it is determined that the virtual reacquisition operation does not need to be performed according to the second offset, the tumor positioning apparatus may output the first accumulated offset, for example, in a display manner. If it is determined that the virtual reacquisition operation needs to be performed according to the second offset, the tumor positioning apparatus may generate a second reference image (i.e., a new reference image re-generated relative to the above first reference image) according to the first accumulated offset, and register the projection images with the second reference image to obtain a third offset, and determine a second accumulated offset. The second accumulated offset is a sum of the first offset, the second offset, and the third offset. When it is determined that the virtual reacquisition operation does not need to be performed according to the third offset, the tumor positioning apparatus may output the second accumulated offset, for example, in the display manner. When it is determined that the virtual reacquisition operation needs to be performed according to the third offset, the tumor positioning apparatus generates a third reference image (i.e., a new reference image re-generated relative to the above second reference image) according to the second accumulated offset, and registers the projection images with the third re-generated reference image to obtain a fourth offset, and so on and so forth.

In the following, an example will be given to illustrate the above method. Assuming that the projection images are KV-level X-ray projection images and the initial reference image includes DRR images, the tumor positioning apparatus may obtain two DRR images according to the CT image in the treatment plan and the preset geometric information, and obtain two KV-level X-ray projection images that are approximately orthogonal. Moreover, the tumor positioning apparatus may also register the KV-level X-ray projection images acquired at the two angles with corresponding DRR images to obtain the first offset, cumulatively display the first offset (an accumulated offset initially obtained by accumulating the first offset and a zero offset initially), and determine whether the virtual reacquisition operation needs to be performed according to the first offset. If the virtual reacquisition operation does not need to be performed, the tumor positioning apparatus outputs the first offset to the control system, and controls the treatment couch to move. If the virtual reacquisition operation needs to be performed, the tumor positioning apparatus may generate two new DRR images according to the first offset, register the KV-level X-ray projection images acquired at the two angles with the corresponding and the generated new DRR images to obtain the second offset, and determine and display the first accumulated offset, that is, the sum of the first offset and the second offset. Then, the tumor positioning apparatus may continue to determine whether the virtual reacquisition operation needs to be performed according to the second offset. If the virtual reacquisition operation does not need to be performed, the first accumulated offset is output in the display manner, and if the virtual reacquisition needs to be performed, two new DRR images are generated according to the first accumulated offset, and so on and so forth.

In the tumor positioning method provided by embodiments of the present disclosure, after the tumor positioning apparatus registers the projection images with the initial reference image to obtain the first offset, the tumor positioning apparatus may generate the first reference image according to the first offset when it is determined that the virtual reacquisition operation needs to be performed, register the projection images with the first generated reference image to obtain the second offset, and output a sum of the first offset and the second offset when it is determined that the virtual reacquisition operation does not need to be performed according to the second offset, that is, output the first accumulated offset, so that the treatment couch is moved according to the first accumulated offset. In this way, time used for generating the new reference image is less than time used for repeatedly obtaining the X-ray projection images at different angles. In embodiments of the present disclosure, when it is determined that the virtual reacquisition operation does not need to be performed according to a corresponding offset (such as the first offset, the second offset, or the third offset, etc.), the position of the tumor is corrected only once according to a corresponding accumulated offset including offset(s) before the offset (such as the initial accumulated offset including the first offset, the first accumulated offset including the first offset and the second offset, or the second accumulated offset including the first offset, second offset, and third offset), for example, the treatment couch is moved only once. In addition, the projection images of the tumor at the different angles are acquired only once. Therefore, compared with a positioning method that repeatedly moves the treatment couch, and repeatedly acquires the X-ray projection images at different angles in the prior art, the tumor positioning method in embodiments of the present disclosure may not only shorten the time for positioning the tumor, but also extends the service life of the treatment couch and the devices such as the detector, and the tube.

Moreover, when it is determined that the virtual reacquisition operation needs to be performed according to the offset, the tumor positioning apparatus generates the new reference image according to the corresponding accumulated offset, and registers the projection images with the generated new reference image. In this way, in a case where the treatment couch is a three-dimensional couch and the offset is any one of the four-dimensional offset, the five-dimensional offset, and the six-dimensional offset, the accumulated offset is considered when the tumor positioning apparatus generates the reference image(s), and the accumulated offset not only includes offset information in the X, Y, and Z directions in the three-dimensional space, but also includes angle information. However, in a process of repeatedly moving the three-dimensional couch in the prior art, the angle information included in the offset cannot be accurately compensated. Therefore, in the embodiments of the present disclosure, the accumulated offset, which the three-dimensional couch is moved according to, is more accurate than an offset in the prior art, which improves an accuracy for positioning the tumor.

Figure 2B:
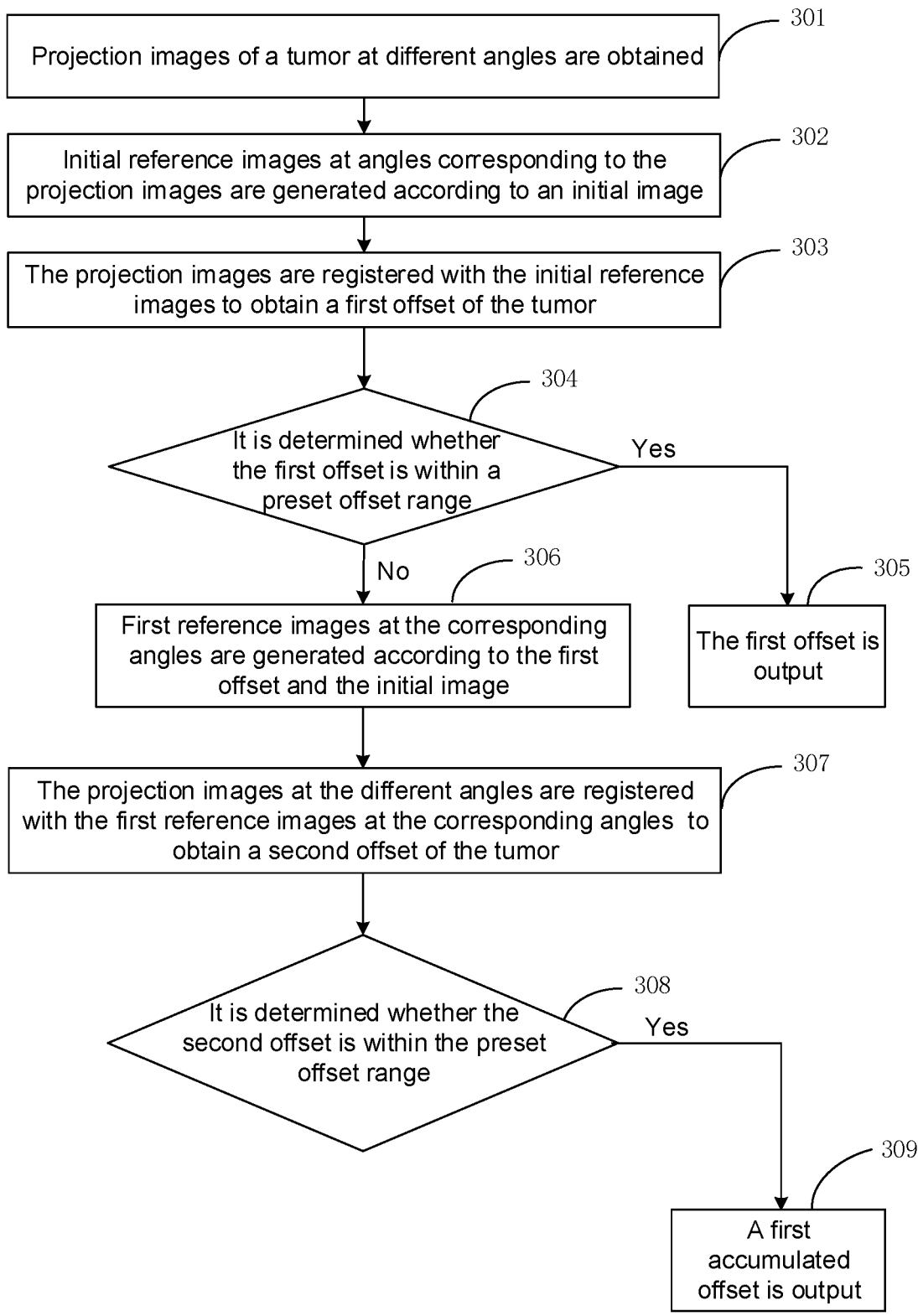
FIG. 2B is a flow diagram of another tumor positioning method, in accordance with embodiments of the present disclosure.
Figure 3:
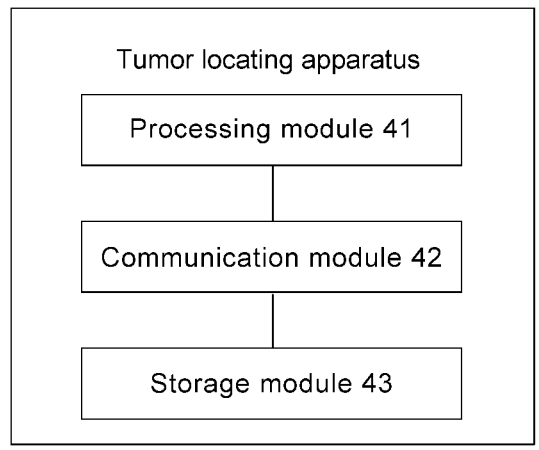
FIG. 3 is a schematic diagram showing components of another tumor positioning apparatus, in accordance with embodiments of the present disclosure.

In order to solve the problems of long time consuming and the service life of the treatment couch and the devices such as the detector, and the tube being reduced due to repeatedly moving the treatment couch and repeatedly acquiring the X-ray projection images at different angles, embodiments of the present disclosure provide another tumor positioning method. As shown in FIG. 2B, the method may include the following steps.

In S301, projection images of a tumor at different angles are obtained.

In S302, initial reference images at angles corresponding to the projection images are generated according to an initial image.

Herein, the initial image includes a three-dimensional CT image, correspondingly, the initial reference images are digitally reconstructured radiograph (DRR) images that are generated according to the CT image, each of which corresponds to a respective one of the projection images at the different angles.

In S303, the projection images are registered with the initial reference images to obtain a first offset of the tumor.

In S304, it is determined whether the first offset is within a preset offset range.

In S305, when the first offset is within the preset offset range, the first offset is output.

In S306, when the first offset is not within the preset offset range, first reference images at corresponding angles are generated according to the first offset and the initial image.

In S307, the projection images at the different angles are registered with the first reference images at the corresponding angles to obtain a second offset of the tumor.

In S308, it is determined whether the second offset is within the preset offset range.

In S309, when the second offset is within the preset offset range, a first accumulated offset is output, the first accumulated offset being a sum of the first offset and the second offset.

Herein, a sequence between S301 and S302 is not limited. For example, S301 may be performed first and then S302 may be performed, or S302 may be performed first and then S301 may be performed, or S301 and S302 may be performed simultaneously.

In the tumor positioning method and the tumor positioning apparatus provided by embodiments of the present disclosure, the projection images are registered with the initial reference images at the corresponding angles to obtain the first offset. After it is determined that the first offset is not in the preset offset range, the first reference images are generated according to the first offset, the projection images are registered with the first reference images to obtain a second offset. After it is determined that the second offset is in the preset offset range, the first accumulated offset, i.e., the sum of the first offset and the second offset is output, thereby moving the treatment couch according to the first accumulated offset.

In an implementation, when the second offset is not within the preset offset range, the above method further includes the following steps.

Second reference images at the corresponding angles are generated according to the first accumulated offset and the initial image.

The projection images at the different angles are registered with the second reference images at the corresponding angles to obtain a third offset of the tumor.

If it is determined that the third offset is within the preset offset range, the method further includes: outputting a second accumulated offset, the second accumulated offset being a sum of the first offset, the second offset and the third offset.

A specific process of the above cycle process may refer to the foregoing description, which will not be described herein again.

The foregoing mainly describes the solution provided by the embodiments of the present disclosure from the tumor positioning apparatus. It will be understood that, in order to realize the above functions, the tumor positioning apparatus includes corresponding hardware structures and/or software modules to perform the functions. Those skilled in the art should easily realize that the present invention may implements the algorithm steps of the examples described in the embodiments disclosed herein in a form of hardware or a combination of hardware and computer software. Whether a function is performed through hardware or a manner of computer software driving the hardware depends on specific application and design constraints of the technical solution. Professional technicians may realize the described functions through different methods for each specific application, but such implementation should not be considered to go beyond the scope of the present invention.

The embodiments of the present disclosure may divide the function modules of the tumor positioning apparatus according to the above methods and examples. For example, different function modules may be divided corresponding to different functions, or two or more functions may be integrated into one processing module. The above integrated modules may be implemented in the form of hardware, or software functional modules. It will be noted that, the division of the modules in the embodiments of the present disclosure is illustrative, and is only a logical function division, and there may be other division manners in actual implementation.

Figure 4:
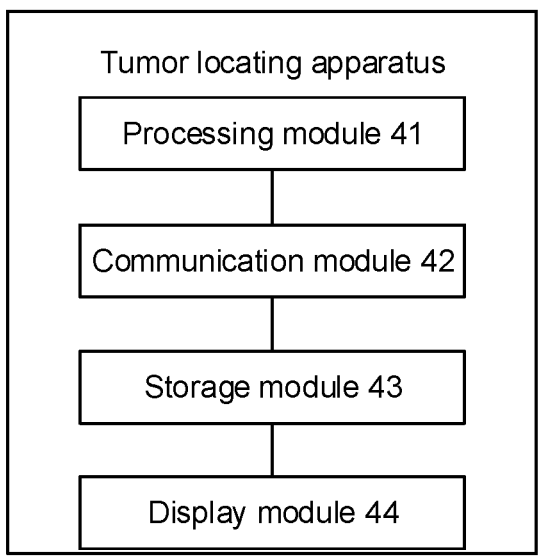
FIG. 4 is a schematic diagram showing components of yet another tumor positioning apparatus, in accordance with embodiments of the present disclosure.

FIG. 4 is a schematic diagram showing components of a tumor positioning apparatus in the above embodiments. As shown in FIG. 4, the tumor positioning apparatus includes: a processing module 41, a communication module 42 and a storage module 43.

The processing module 41 is configured to control and managing actions of the tumor positioning apparatus. For example, the processing module 41 is used for supporting the tumor positioning apparatus to perform the step 201, the steps in FIG. 2A, the steps in FIG. 2B, and/or used for other processes of technologies described herein. The communication module 42 is configured to support the tumor positioning apparatus to communicate with and other network entities. The storage module 43 is configured to store program codes and data of the tumor positioning apparatus.

The processing module 41 may be the processor in FIG. 1. The processing module 41 may implement or execute various exemplary logical blocks, modules and circuits described in embodiments of the present disclosure. The processor may also be a combination of realizing computing functions. For example, the processor may be a combination of one or more microprocessors, or a combination of DSP and microprocessor. The communication module 42 may be the communication interface in FIG. 1. The storage module 43 may be the memory in FIG. 1.

It will be noted that, all relevant contents of the steps involved in the above methods and embodiments may be cited in the functional description of the corresponding functional modules, which will not be repeated here.

The tumor positioning apparatus provided in embodiments of the present disclosure may be configured to perform the above tumor positioning methods. Therefore, it may achieve the same effect as the above tumor positioning method.

Further, in embodiments of the present disclosure, as shown in FIG. 5, the tumor positioning apparatus may further include a display module 44.

The display module 44 is configured to support the tumor positioning apparatus to perform the step of displaying the accumulated offset (such as the initial accumulated offset, the first accumulated offset or the second accumulated offset) in the tumor positioning method shown in FIG. 2A or 2B. The display module 44 communicates with the processing module 41 to display the corresponding accumulated offset from the processing module 41. The display module 44 may is, for example, any device with a display function such as a display.

Through the description of the above embodiments, those skilled in the art will be clearly understood that, for the convenience and brevity of description, only the division of the above functional modules is used as an example. In practical applications, the above functions may be allocated to different functional modules according to needs. That is, the internal structure of the apparatus may be divided into different functional modules to complete all or part of the functions described above.

In the embodiments provided in the present disclosure, it will be understood that the disclosed apparatus and method may be implemented through other manners. For example, the embodiments about the apparatus described above are only illustrative. For example, the division of the module or unit is only a logical function division, and there may be other division manners in actual implementation. For example, multiple units or components may be combined or integrated into another device, or some features may be omitted or not performed. In addition, the displayed or discussed mutual coupling or direct coupling or communication connection may be indirect coupling or communication connection through some interfaces, devices or units, or may be in electrical, mechanical or other forms.

The units described as separate components may or may not be physically separated, and the component displayed as a unit may be one physical unit or multiple physical units. That is, the component(s) may be located in one place, or may be distributed at many different places. Some or all of the units may be selected to achieve the purpose of the solutions of the embodiments according to actual needs.

In addition, the functional units in the embodiments of the present disclosure may be integrated into one processing unit, or each unit may exist alone physically, or two or more units may be integrated into one unit. The integrated unit may be implemented in a form of hardware or software functional unit.

When the integrated unit is realized in the form of the software functional unit and sold or used as an independent product, it may be stored in the readable storage medium. Based on this understanding, the technical solutions of the embodiments of the present disclosure or a part of the technical solutions that contribute to the prior art, or all or part of the technical solutions may be embodied in the form of software products. The software product is stored in a storage medium and includes many instructions to enable a device (such as a single-chip microcomputer or a chip) or a processor to execute all or part of the steps of the method in the embodiments of the present disclosure. The storage media include: a U disk, a mobile hard disk, a ROM, a RAM, a magnetic disk or an optical disk and other media that may store program codes.

The foregoing descriptions are merely specific implementation manners of the present invention, but the protection scope of the present invention is not limited thereto, and the changes or replacements within the technical scope disclosed by the present invention should be within the protection scope of the present invention. Therefore, the protection scope of the present invention shall be subject to the protection scope of the claims.

What is claimed is:

1. A tumor positioning method, comprising:
    obtaining projection images of a tumor at different angles; and
    registering the projection images with an initial reference image to obtain a first offset of the tumor, wherein
    if it is determined that a virtual reacquisition operation needs to be performed according to the first offset, the method further comprises:
    generating a first reference image according to the first offset; and
    registering the projection images with the first reference image to obtain a second offset of the tumor;
    if it is determined that the virtual reacquisition operation does not need to be performed according to the second offset, the method further comprises:
    outputting a first accumulated offset, the first accumulated offset being a sum of the first offset and the second offset.

2. The tumor positioning method according to claim 1, wherein if it is determined that the virtual reacquisition operation needs to be performed according to the second offset, the method further comprises:
    generating a second reference image according to a first accumulated offset, the first accumulated offset being a sum of the first offset and the second offset; and
    registering the projection images with the second reference image to obtain a third offset of the tumor;
    if it is determined that the virtual reacquisition operation does not need to be performed according to the third offset, the method further comprises:
    outputting a second accumulated offset, the second accumulated offset being a sum of the first offset, the second offset and the third offset.

3. The tumor positioning method according to claim 2, wherein determining that the virtual reacquisition operation needs to be performed includes:
    determining that an offset is not within a preset offset range, or receiving an instruction that it is determined that the virtual reacquisition operation needs to be performed according to the offset, wherein
    the offset is the first offset, the second offset or the third offset.

4. The tumor positioning method according to claim 2, after determining an accumulated offset, the method further comprising:
    displaying the accumulated offset, wherein
    the accumulated offset is the first accumulated offset or the second accumulated offset.

5. The tumor positioning method according to claim 2, wherein generating the second reference image includes:
    generating the second reference image through a preset algorithm according to the first accumulated offset and pre-stored geometric information.

6. The tumor positioning method according to claim 1, wherein generating the first reference image includes:
    generating the first reference image through a preset algorithm according to the first offset and pre-stored geometric information.

7. The tumor positioning method according to claim 1, wherein the initial reference image includes a computed tomography (CT) image;
    registering the projection images with the initial reference image to obtain the first offset includes:
    reconstructing the projection images at the different angles to obtain a target image with same dimensions as the CT image; and
    registering the target image with the CT image to obtain the first offset.

8. The tumor positioning method according to claim 1, wherein the initial reference image includes digitally reconstructed radiograph (DRR) images each corresponding to a respective one of the projection images at the different angles;
    registering the projection images with the initial reference image to obtain the first offset includes:
    registering the projection images with the DRR images to obtain two-dimensional offsets of the tumor; and
    obtaining the first offset according to the two-dimensional offsets.

9. The tumor positioning method according to claim 1, further comprising:
    obtaining the initial reference image before obtaining the projection images.

10. A tumor positioning apparatus, comprising: a processor and a memory, wherein
    the memory is configured to store computer execution instructions, and when the tumor positioning apparatus is running, the processor is configured to execute the computer execution instructions stored in the memory to cause the tumor positioning apparatus to perform the tumor positioning method according to claim 1.

11. A non-transitory computer-readable storage medium storing computer execution instructions that, when executed by a computer, cause the computer to perform the tumor positioning method according to claim 1.

12. A tumor positioning method, comprising:
    obtaining projection images of a tumor at different angles;

generating initial reference images at angles corresponding to the projection images according to an initial image; and registering the projection images with the initial reference images to obtain a first offset of the tumor, wherein if it is determined that the first offset is not within a preset offset range, the method further comprises:

generating first reference images at corresponding angles according to the first offset and the initial image; and registering the projection images at the different angles with the first reference images at the corresponding angles to obtain a second offset of the tumor;

if it is determined that the second offset is within the preset offset range, the method further comprises:

outputting a first accumulated offset, the first accumulated offset being a sum of the first offset and the second offset.

13. The tumor positioning method according to claim 12, wherein if it is determined that the second offset is not within the preset offset range, the method further comprises:

generating second reference images at the corresponding angles according to the first accumulated offset and the initial image; and registering the projection images at the different angles with the second reference images at the corresponding angles to obtain a third offset of the tumor;

if it is determined that the third offset is within the preset offset range, the method further comprises:

outputting a second accumulated offset, the second accumulated offset being a sum of the first offset, the second offset and the third offset.

14. The tumor positioning method according to claim 12, wherein the initial image includes a computed tomography (CT) image; and the initial reference images are digitally reconstructured radiograph (DRR) images each corresponding to a respective one of the projection images at the different angles.

* * * * *